United States Patent
Fuentes

(10) Patent No.: US 10,195,461 B2
(45) Date of Patent: Feb. 5, 2019

(54) PARTICLE THERAPY APPARATUS FOR EYE TREATMENT

(71) Applicant: Ion Beam Applications S.A., Louvain-la-Neuve (BE)

(72) Inventor: Carolina Fuentes, Essen (DE)

(73) Assignee: Ion Beam Applications S.A., Louvain-la-Neuve (BE)

( * ) Notice: Subject to any disclaimer, the term of this patent is extended or adjusted under 35 U.S.C. 154(b) by 0 days.

(21) Appl. No.: 15/835,980

(22) Filed: Dec. 8, 2017

(65) Prior Publication Data
US 2018/0161595 A1    Jun. 14, 2018

(30) Foreign Application Priority Data

Dec. 8, 2016 (EP) .................................. 16202959.9

(51) Int. Cl.
*A61N 5/00* (2006.01)
*A61N 5/10* (2006.01)
(Continued)

(52) U.S. Cl.
CPC .......... *A61N 5/1017* (2013.01); *A61B 3/0083* (2013.01); *A61B 3/0091* (2013.01); *A61B 3/145* (2013.01); *A61F 9/007* (2013.01); *A61N 5/1043* (2013.01); *A61N 5/1047* (2013.01); *A61N 5/1049* (2013.01); *A61N 5/1081* (2013.01); *A61B 2090/3937* (2016.02);
(Continued)

(58) Field of Classification Search
CPC .. A61N 5/1017; A61N 5/1043; A61N 5/1047; A61N 5/1049; A61N 5/1081; A61B 3/0083; A61B 3/0091; A61B 3/145; A61B 2090/3937; A61F 9/007

USPC ................ 250/492.1, 492.2, 492.3
See application file for complete search history.

(56) References Cited

U.S. PATENT DOCUMENTS

| 6,134,294 A | 10/2000 | Gibbs |
| 2009/0182310 A1 | 7/2009 | Gertner et al. |
| 2015/0157879 A1 | 6/2015 | Wu et al. |

FOREIGN PATENT DOCUMENTS

WO    WO-2008/118198    10/2008

OTHER PUBLICATIONS

Hartsell, W. et al. (May 2016). "Feasibility of Proton Beam Therapy for Ocular Melanoma Using a Novel 3D Treatment Planning Technique," *International Journal of Radiation: Oncology Biology Physics*, vol. 95, No. 1; pp. 353-359.
(Continued)

*Primary Examiner* — Nicole Ippolito
*Assistant Examiner* — Hanway Chang
(74) *Attorney, Agent, or Firm* — Finnegan, Henderson, Farabow, Garrett & Dunner LLP

(57) ABSTRACT

A particle therapy apparatus for irradiating a diseased part of a patient's eye with a charged particle beam comprises a particle accelerator to generate the particle beam, a movable irradiation nozzle adapted to direct the particle beam towards the patient's eye according to different beam directions, and a patient support adapted to receive and hold the patient in a treatment position. The apparatus further comprises a pencil beam scanning subsystem configured to scan the particle beam over the diseased part of the patient's eye, a movable marker arranged in such a way that it is visible by the patient while he is in the treatment position and a controller configured to move said marker to a pre-determined and patient-specific position before starting an irradiation of the eye with the particle beam.

15 Claims, 3 Drawing Sheets

Figure 1:
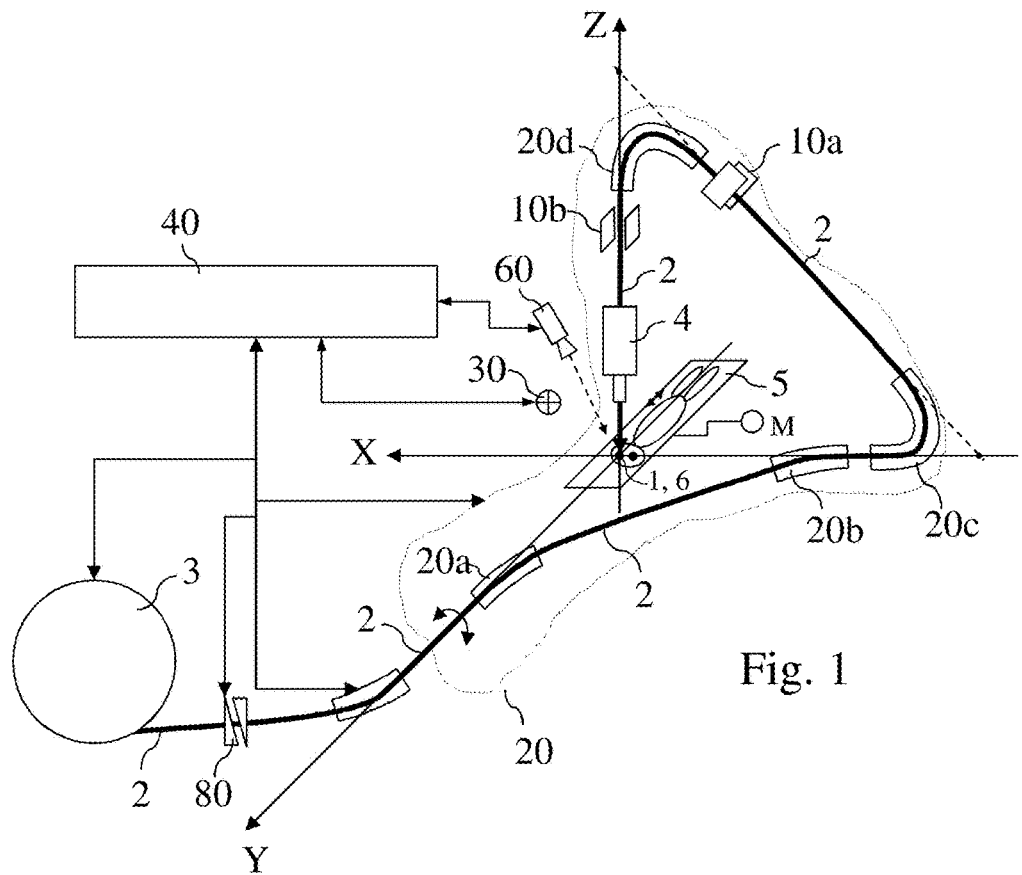

(51) Int. Cl.
*A61B 3/00* (2006.01)
*A61F 9/007* (2006.01)
*A61B 3/14* (2006.01)
*A61B 90/00* (2016.01)

(52) U.S. Cl.
CPC ..... *A61B 2090/3945* (2016.02); *A61N 5/1071* (2013.01); *A61N 2005/1051* (2013.01); *A61N 2005/1059* (2013.01); *A61N 2005/1074* (2013.01); *A61N 2005/1087* (2013.01)

(56) References Cited

OTHER PUBLICATIONS

European Search Report completed May 5, 2017, in counterpart EP Application No. 16 20 2959; 5 pages.

PARTICLE THERAPY APPARATUS FOR EYE TREATMENT

CROSS-REFERENCE TO RELATED PATENT APPLICATIONS

This application claims the benefit of a European Application No. EP 16202959.9, filed Dec. 8, 2016, which is hereby incorporated by reference in its entirety.

FIELD OF THE INVENTION

The invention relates to an apparatus for irradiating a diseased part of an eye of a patient with a charged particle beam for therapy purposes.

BACKGROUND OF THE INVENTION

Particle therapy, for example proton therapy, has been used for over 40 years to treat ocular melanoma.

Due to the specific nature of an eye and of ocular melanoma, particle therapy apparatus which are known for treating such diseases are generally making use of a dedicated single, anterior, and fixed beam line, with a dedicated nozzle having a small aperture. They use beam scattering techniques to deliver a broad beam for covering the target volume to be irradiated. A drawback of these apparatus is that dedicated equipment must be designed, manufactured, installed and operated, and that such dedicated apparatus cannot or can hardly be used for treating other types of tumors of a human body. A further drawback is that such apparatus may cause unwanted neutron and/or gamma ray radiation towards the patient because of the presence of beam scattering elements in the beamline and in the line of sight of the patient.

Another type of particle therapy apparatus for treating ocular melanoma is known from William F. Hartsell et al. in "Feasibility of Proton Beam Therapy for Ocular Melanoma Using a Novel 3D Treatment Planning Technique" (International Journal of Radiation Oncology*Biology*Physics, Volume 95, Issue 1, 1 May 2016, Pages 353-359, Particle Therapy Special Edition). This apparatus does not make use of a fixed beam line but rather makes use of a rotating gantry to direct the particle beam according to three different directions towards the target to be treated, so that the target will be irradiated with three different (generally coplanar) fields in the course of the treatment. A drawback of such apparatus is that it requires a relatively long treatment time, which is far from convenient for eye treatment and which also constitutes an economic disadvantage. Such apparatus also uses broad beam techniques to cover the target volume, such as the known wobbling technique for example. Hence, conformity of the actual received dose with a planned dose may not be optimal. Dose rates may also be insufficient with such techniques, which further impairs on treatment time.

SUMMARY OF THE INVENTION

It is an object of the invention to address the problems of the state of the art particle therapy apparatus. It is more particularly an object of the invention to provide particle beam therapy apparatus which is adapted to treat a diseased part of an eye of a human or animal body, and which enables shorter treatment times than known apparatus of this type, yet remaining substantially adapted to treat other diseased parts of a human or animal body than an eye.

The invention is defined by the independent claims. The dependent claims define advantageous embodiments.

According to the invention, there is provided a particle therapy apparatus for irradiating a diseased part of a patient's eye with a charged particle beam, the particle therapy apparatus comprising:
- a particle accelerator to generate the charged particle beam,
- a movable irradiation nozzle adapted to receive and direct the charged particle beam towards the patient's eye according to different beam directions,
- a patient support adapted to receive and hold the patient in a treatment position,
- a movable marker arranged in such a way that it is visible by the patient while the patient is in the treatment position,
- a controller configured to move said marker to a predetermined and patient-specific position before an irradiation of the diseased part of the patient's eye with the charged particle beam, and
- a pencil beam scanning subsystem configured to scan the charged particle beam over the diseased part of the patient's eye.

With the term "patient", one must understand a living being such as human person or an animal.

Compared to the use of a fixed and dedicated eye beam line, an apparatus according to the invention allows to treat not only eye s but also other diseased parts of a patient, yet with limited or no changes to the hardware of the apparatus. It also allows to reduce neutron and/or gamma radiation towards the patient, or even to limit these to negligible quantities (in terms of effects to the patient), because it doesn't have significant sources emitting neutrons and/or gamma rays in a main direction towards the patient.

Compared to the apparatus of William F. Hartsell et al., an apparatus according to the invention allows to considerably reduce the treatment time of the patient because of the presence of a pencil beam scanning system and the possibility to deliver higher dose rates, yet allowing for a more targeted irradiation with less side effects. Reducing the treatment time of the patient both contributes to a better comfort for the patient and to economic and social advantages since it allows to treat more patients per unit of time and per apparatus.

Preferably, the therapy apparatus comprises an isocentric gantry rotatable about an axis Y, said gantry comprising a sequence of bending magnets arranged along a beam path to receive the particle beam along the axis Y, to first bend the particle beam away from the axis Y and to finally bend and direct the particle beam back towards the axis Y, and the irradiation nozzle is arranged on said gantry and downstream of a last bending magnet of said sequence of bending magnets. Such a gantry is currently commonly used for treating diseased parts of a patient other than an eye, but—thanks to its additional features such as the movable marker—it can now also be used for treating ocular melanoma for instance. Hence, a dedicated beam eye line becomes unnecessary, thereby saving costs and space.

Preferably, the pencil beam scanning subsystem is a spot scanning type subsystem. Preferably the particle therapy apparatus is configured to perform a complete irradiation treatment of the diseased part of the patient's eye with a single nominal beam direction with respect to a single direction of the optical axis of the patient's eye. This allows to further reduce the treatment time of the patient, particularly compared to the apparatus of William F. Hartsell et al. which requires irradiation according to three different irradiation fields, which requires rotating the gantry to three different angular positions with interruption of the particle beam between each two successive positions.

The movable marker may be mechanically linked to the patient support, or to a floor supporting the particle therapy apparatus. Preferably, the movable marker is mechanically linked to the irradiation nozzle, because this allows to reduce its required moving range compared to the previous two solutions, thus making it simpler, cheaper and less bulky.

Preferably, the particle accelerator is a cyclotron or a synchrotron. Preferably, the particle beam is a beam of electrically charged particles excluding electrons, such as protons or carbon ions for example.

SHORT DESCRIPTION OF THE DRAWINGS

Figure 2:
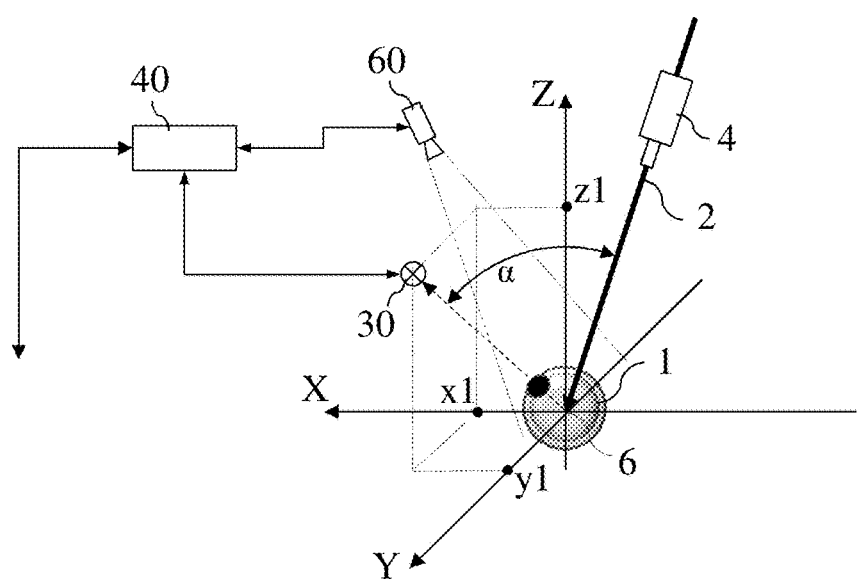
Figure 3:
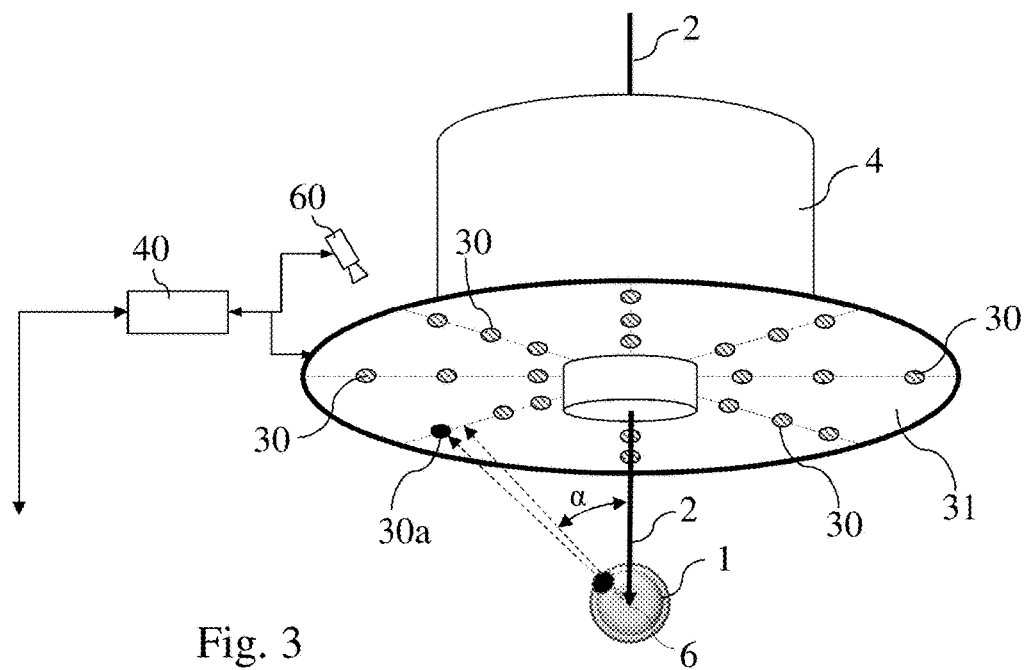
Figure 4:
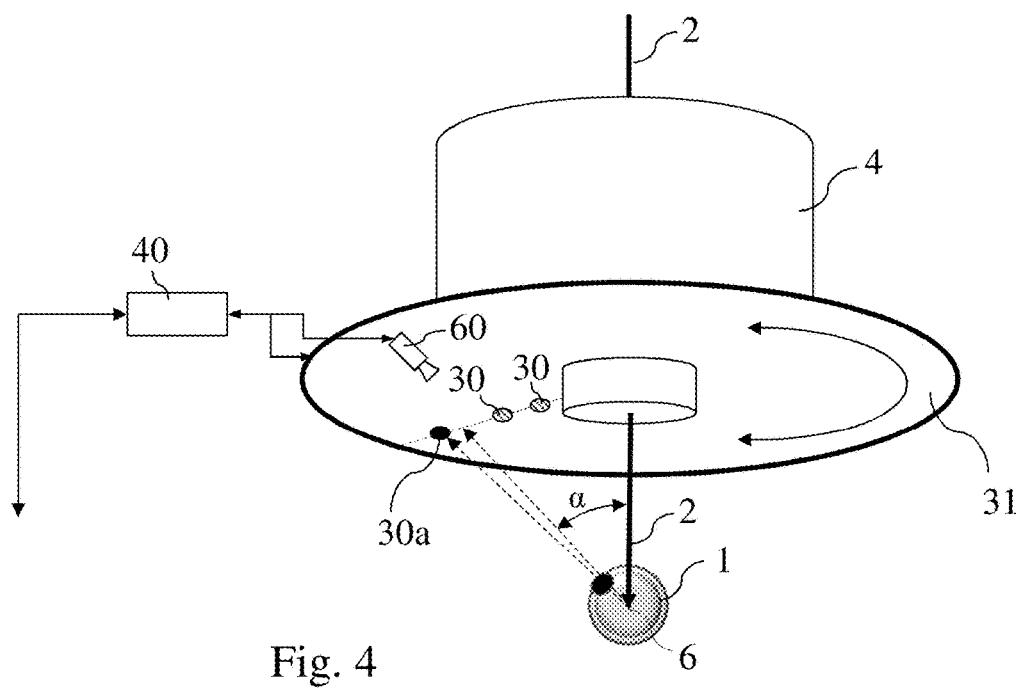
Figure 5:
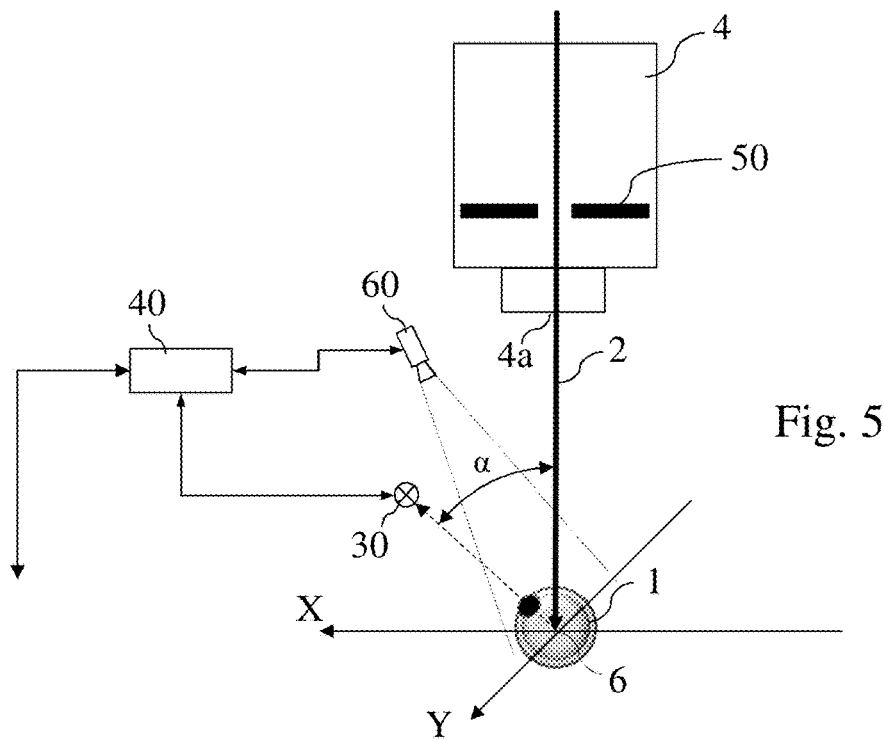
Figure 6:
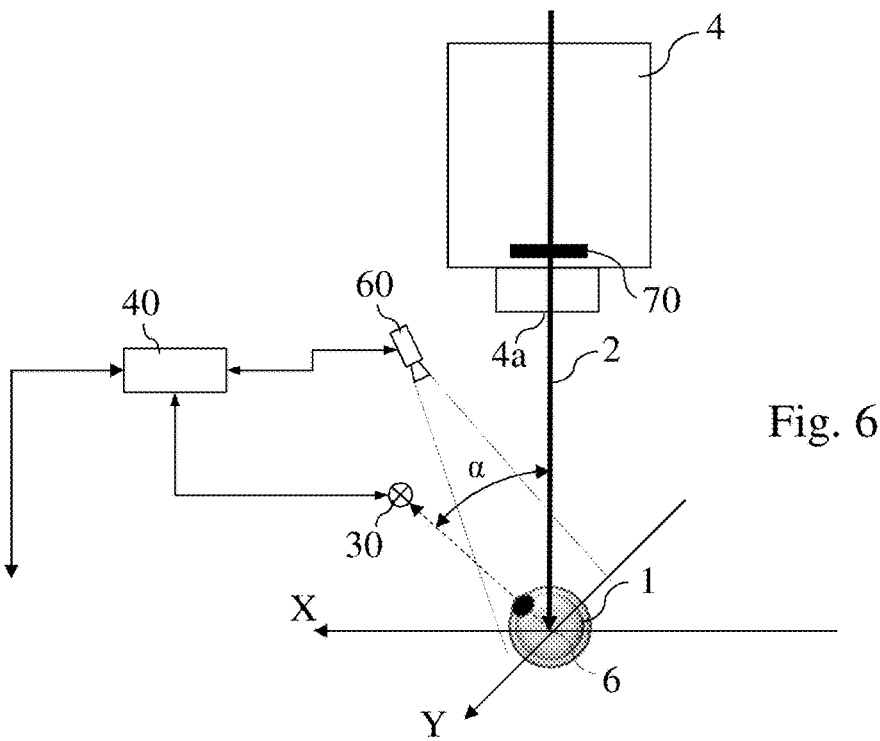

These and further aspects of the invention will be explained in greater detail by way of examples and with reference to the accompanying drawings in which:

FIG. 1 schematically shows a particle therapy apparatus according to the invention;

FIG. 2 schematically shows a more detailed view of a part of the apparatus of FIG. 1;

FIG. 3 schematically shows a more detailed view of a part of the apparatus of FIG. 1 in a preferred embodiment;

FIG. 4 schematically shows a more detailed view of a part of the apparatus of FIG. 1 in another preferred embodiment;

FIG. 5 schematically shows a more detailed view of a part of the apparatus of FIG. 1 in another preferred embodiment;

FIG. 6 schematically shows a more detailed view of a part of the apparatus of FIG. 1 in another preferred embodiment;

The drawings of the figures are neither drawn to scale nor proportioned. Generally, similar or identical components are denoted by the same reference numerals in the figures.

DETAILED DESCRIPTION OF EMBODIMENTS OF THE INVENTION

FIG. 1 schematically shows an exemplary particle therapy apparatus according to the invention. It is configured for irradiating a diseased part of a patient's eye (1) with a charged particle beam (2). The particle therapy apparatus comprises a particle accelerator (3) to generate the charged particle beam (2), a movable irradiation nozzle (4) adapted to receive and direct the charged particle beam (2) towards the patient's eye (1) according to different beam directions, and a beam transport system to transport the particle beam from the particle accelerator (3) to a beam entry point into the nozzle (4).

There are several known devices to move such an irradiation nozzle (4) with respect to a target (here with respect to the eye (1) of the patient). One known device is for example disclosed in patent publication number WO2016/029083 wherein the nozzle (4) can be moved to four different positions and orientations in order to irradiate a target according to four different orientations with respect to said target (see for example FIGS. 2A to 2E of this document).

Preferably, and as shown on FIG. 1, the particle therapy apparatus according to the invention comprises an isocentric gantry (20) rotatable about an axis Y, said gantry (20) comprising a sequence of bending magnets (20a, 20b, 20c, 20d) arranged along a beam path to receive the particle beam (2) along the axis Y, to first bend the particle beam (2) away from the axis Y and to finally bend and direct the particle beam (2) back towards the axis Y. In that case, the irradiation nozzle (4) is fixed on said gantry (20) and downstream of a last bending magnet (20d) of said sequence of bending magnets, so that the irradiation nozzle (4) will rotate with the gantry (20). The nozzle (4) will hence be able to direct the charged particle beam (2) towards the patient's eye (1) according to different beam directions which all cross at a common location, usually called the isocentre (6). On FIG. 1, the isocentre (6) corresponds to the origin of the shown XYZ referential.

The particle therapy apparatus also comprises a patient support (5) which is adapted to receive and hold the patient in a treatment position. The treatment position is the position of the patient when ready for starting the irradiation of the diseased part of his eye (1) with the particle beam (2). In case an isocentric gantry (20) is used, the treatment position is generally a position of the patient wherein the diseased part of his eye (1) is located at or close to the isocentre (6), as shown on FIG. 1.

In the example of FIG. 1, the patient support (5) is a couch adapted to receive and hold the patient in a supine treatment position, namely a position wherein his coronal plane is parallel or coincident with the XY or horizontal plane and wherein the patient is looking upwards.

Alternatively, the patient support (5) may be adapted to receive and hold the patient in a seated treatment position. The patient support (5) can in this case be a seat for example. The seat is preferably placed in such a way that the sagittal plane of the patient is perpendicular to the Y axis when the patient is in the said seated treatment position.

The particle therapy apparatus also comprises a movable marker (30) arranged in such a way that it is visible by the patient while the patient is in the treatment position, and a controller (40) configured to move said marker (30) to a pre-determined and patient-specific position before an irradiation of the diseased part of the patient's eye (1) with the charged particle beam (2).

The purpose of these latter two features is to reduce the risk of irradiating healthy tissues of the patient by irradiating the diseased part of the patient's eye (1) under an appropriate particle beam (2) angle. A specific purpose may for example be to reduce the irradiation dose to the iris and/or the cornea and/or ciliary body, and/or other organs at risk of the patient.

Preferably, the movable marker (30) comprises a light source, preferably a point source. More details concerning the movable marker (30) and the controller (40) will be given in relation to FIG. 2 and FIG. 3.

The particle therapy apparatus further comprises a pencil beam scanning subsystem configured to scan the charged particle beam (2) over the diseased part of the patient's eye (1). In the example of FIG. 1, the pencil beam scanning subsystem comprises a first beam scanner (10a) arranged upstream of the last bending magnet of the gantry (20) and configured to scan the particle beam (2) according to a first direction (for example the X direction) over the diseased part of the patient's eye (1), and a second beam scanner (10b) arranged downstream of the last bending magnet of the gantry (20) and configured to the scan the particle beam (2) according to a second direction (generally perpendicular to the first direction; for example the Y direction) over the diseased part of the patient's eye (1). It will be obvious that many other scanner configurations may be used. Given the relatively small scanning angles required for treating a diseased part of the patient's eye (1), the first and second beam scanners (10a, 10b) may alternatively be both located upstream of the last bending magnet (20d) of the gantry (20), or they may be both located downstream of the last bending magnet (20d) of the gantry (20), such as in the irradiation nozzle (4) for example.

The particle beam (2) may be raster-scanned or spot-scanned over the target. Preferably, the pencil beam scanning subsystem is a spot scanning type subsystem. With spot scanning—and in contrast to raster scanning—the particle beam (2) is switched off between two consecutive spots (sometimes called "voxels") of the target to be irradiated with the scanned particle beam (2). Preferably, the pencil beam scanning subsystem comprises means to modulate the intensity of the particle beam (2) (corresponding to what is sometimes referred to as Intensity Modulated Proton Therapy or IMPT).

As such, pencil beam scanning, spot scanning and IMPT are all well known in the art of particle therapy (see for example B. Marchand et al. in "*IBA proton pencil beam scanning: an innovative solution for cancer treatment*"; Proceedings of EPAC 2000, Vienna, Austria, pp 2539 sq., and Faiz M. Khan in "*The physics of Radiation Therapy*"—fourth edition—Wolters Kluwer, pp 521 sq.), and will therefore not be described in further detail here.

Preferably, the therapy apparatus according to the invention is configured to perform a complete irradiation treatment of the diseased part of the patient's eye (1) with a single nominal particle beam direction with respect to a single direction of the optical axis of the patient's eye (1). This more specifically contributes to reducing the treatment time. By nominal particle beam direction, one shall understand the direction of the particle beam (2) when exiting from the irradiation nozzle (4) and when the particle beam (2) is unscanned (all beam scanning magnets being switched OFF).

FIG. 2 schematically shows a more detailed view of a part of the apparatus of FIG. 1 wherein the pre-determined and patient-specific position of the marker (30) is a point of coordinates (x1, y1, z1) in the XYZ referential, wherein the controller (40) has moved the movable marker (30) to said point (x1, y1, z1), wherein the patient is in the treatment position and wherein he is gazing with his diseased eye (1) at said marker (30) so that the optical axis of his diseased eye (1) is making an angle α (alpha) with the (planned) direction of the particle beam (2) as defined by the position and orientation of the irradiation nozzle (4). This is of course all done before starting a treatment irradiation of the patient's eye (1). The predetermination of the coordinates (x1, y1, z1) may for example be performed by a medical doctor and/or by the said controller (40) and/or by another controller (40) on the basis of 3D images of the diseased eye (1) of the patient, such as CT and/or MRI images for example. Once they are determined, these coordinates are transferred to or used by the said controller (40) in order that the said controller (40) can and does move the marker (30) to the point having these coordinates (x1, y1, z1). Once the marker (30) is placed at the point having these coordinates (x1, y1, z1), the patient is of course instructed to gaze at said marker (30) before starting the treatment irradiation of his diseased eye (1). One may for example make use of the OID device and methods disclosed in William F. Hartsell et al. in "Feasibility of Proton Beam Therapy for Ocular Melanoma Using a Novel 3D Treatment Planning Technique" (International Journal of Radiation Oncology*Biology*Physics, Volume 95, Issue 1, 1 May 2016, Pages 353-359, Particle Therapy Special Edition).

The movable marker (30) may for example be a light source such as a LED for example, or a small object which the patient can identify and distinguish from other parts of the particle therapy apparatus or from other objects in his field of view while he is in the treatment position. Identification generally results from an information given to the patient about the nature and the function of the marker (30).

Alternatively, the movable marker (30) may for example comprise a light source coupled to one end of an optical fiber (or bundle of optical fibers), the opposite end (tip) of said optical fiber (bundle) being movable to the said pre-determined and patient-specific position. Movement of the marker (30) can be done with any appropriate drive assembly (not shown on the figures for the sake of clarity) operated by the controller (40).

The movable marker (30) may be mechanically linked to the patient support (5), or to a floor supporting the particle therapy apparatus. Preferably, the movable marker (30) is mechanically linked to the irradiation nozzle (4), because this allows to reduce its required moving range compared to the previous two solutions, thus making it simpler, cheaper and less bulky. In this latter case, the drive assembly is preferably attached to the irradiation nozzle (4) or to a structure bearing said irradiation nozzle (4) such as the rotating gantry (20) for example.

Instead of having a marker (30) which is mechanically movable to various positions in space, one may alternatively have a plurality of individually addressable light sources arranged at various positions in space, and have the controller (40) configured to address (i.e. to light up) that one of these light sources whose position in space corresponds to the said pre-determined and patient-specific position. Hence, the movable marker (30) must be understood as being a marker (30) which is mechanically movable to various patient-identifiable positions or as being a marker (30) whose patient-identifiable position can be varied.

FIG. 3 schematically shows a more detailed view of a part of the apparatus of FIG. 1 in a preferred embodiment wherein the marker is mechanically linked to the irradiation nozzle (4) and wherein patient-identifiable positions of said marker (30) can be varied. In this example, the irradiation nozzle (4) comprises a disk (31) whose plane is perpendicular to the central axis of the irradiation nozzle (4). Said disk (31) holds a plurality of individual light sources (30) such as LEDs for example, arranged in a 2D matrix and functionally forming said movable marker. The controller (40) is operatively connected to each of these light sources (30) and is configured so as to be able to light up individually any of them. The controller (40) is further configured to light-up that one of these light sources whose position in space best corresponds to the said pre-determined and patient-specific position. In the example of FIG. 3, the controller (40) will for example light up light source 30a. Needless to say, the smaller the pitch between two adjacent light sources, the higher the accuracy of the device. It will moreover be obvious that other shapes than a disk can be used and that other matrix arrangements of the light sources can be used as well. Alternatively, a "hybrid" marker may be used, namely a marker which is mechanically movable and whose movable part comprises a plurality of individually addressable light sources, so as to be able to change the position of the marker by combining a mechanical movement of its movable part and an addressing of an individual light source. FIG. 4 shows an exemplary embodiment thereof. It is similar to the embodiment of FIG. 3, except that the disk (31) is rotatable about its axis with respect to the irradiation nozzle (4), and except that the said disk (31) holds a plurality of individually addressable light sources (30) arranged only along one radius of the disk (31). The controller (40) is in such case further configured to drive the disk (31) into rotation by a selectable angle. In the example of FIG. 4, the controller (40) will for example rotate the disk to the illustrated angular position and light up light source 30*a*.

Preferably, the irradiation nozzle (4) comprises a collimator (50) in order to reduce a lateral penumbra in the patient's eye (1). An exemplary embodiment of such a nozzle (4) is shown in FIG. 5. Preferably, the collimator (50) is configured to limit the lateral penumbra at the level of the target to a maximum of 2.5 mm (taken between 20% and 80% of the delivered dose), preferably to a maximum of 2 mm (taken between 20% and 80% of the delivered dose). Preferably the collimator (50) has an inner diameter comprised between 0.5 cm and 3 cm, more preferably between 1 cm and 2.5 cm.

Preferably, the irradiation nozzle (4) comprises an energy absorber (70) arranged across the particle beam (2) path to reduce the energy of the particle beam (2). An exemplary embodiment of such a nozzle (4) is shown in FIG. 6. Placing such an energy absorber (70) across the beam path in the nozzle (4) is useful in case the particle accelerator (3) has a lower limit of particle beam (2) energy which is too high for treating a patient's eye (1). A conventional cyclotron used for particle therapy purposes and provided with a main energy degrader (80) (sometimes referred to as an Energy Selection System) for varying the energy of the particle beam (2) has for example a minimum beam energy of approximately 70 MeV a the output of the main energy degrader (80), which would result in a too large beam penetration depth of about 4 cm in the patient. The same drawback exists with synchrotrons designed and used for particle therapy purposes.

Preferably, the energy absorber (70) is configured to reduce the energy of the charged particle beam (2) to less than 70 MeV, more preferably to less than 60 MeV, more preferably to less than 50 MeV, more preferably to less than 40 MeV, more preferably to less than 30 MeV, as measured at an output (4*a*) of the nozzle (4). In case of a beam of protons, the energy absorber (70) is more preferably configured to reduce the energy of the charged particle beam (2) to an energy comprised in the range of 15 MeV to 25 MeV, even more preferably to an energy comprised in the range of 20 MeV to 22 MeV, as measured at an output (4*a*) of the nozzle (4).

The energy absorber (70) may for example be a plate of Poly(methyl methacrylate) (sometimes referred to as PMMA or acrylic glass) of appropriate thickness to achieve the desired energy attenuation.

In case the nozzle (4) comprises a collimator (50), as shown in FIG. 5 for example, the energy absorber (70) may be placed upstream or downstream of the said collimator (50) along the beam path in the irradiation nozzle (4). Preferably, the energy absorber (70) is placed in the irradiation nozzle (4) and upstream of the said collimator (50).

As shown on FIGS. 1 to 6, the particle therapy apparatus preferably further comprises a video camera (60) placed in such a way that a field of view of said camera (60) covers at least the diseased patient's eye (1) when the patient is in the treatment position, and the controller (40) is further configured to acquire images from said video camera (60) and to monitor the position and/or orientation of the diseased patient's eye (1) in real time while the patient is in the treatment position. Monitoring the position and/or orientation of the diseased patient's eye (1) can for example be achieved by monitoring in real time the position of the image of the said eye's pupil on the camera's total image. The camera (60) may be mounted fixedly with respect to the floor on which the particle therapy apparatus is mounted, or it may be mounted to the irradiation nozzle (4) or to a structure supporting the irradiation nozzle (4) so as to move with the irradiation nozzle (4). In case the marker (30) is mechanically movable, as in the embodiment of FIG. 4 for example, the camera (60) may alternatively also be mounted on the marker (30) so as to move with the marker (30).

More preferably, the controller (40) is further configured to monitor the position and/or orientation of the patient's eye (1) before starting irradiation of the diseased part of the patient's eye (1) with the particle beam (2), and to start said irradiation only when the controller (40) detects or determines that the marker (30) is placed at the pre-determined and patient-specific position and that the diseased patient's eye (1) is gazing at said marker (30). Detecting that the marker (30) is placed at the pre-determined and patient-specific position can for example be done by using known closed loop controls in case the marker (30) is at least partially moved mechanically. In case the marker (30) is not moved mechanically, as illustrated in FIG. 3 for example, the controller (40) determines that the marker (30) is at the pre-determined and patient-specific position right after having addressed the appropriate light source. Starting irradiation can for example be done by switching ON the particle beam (2) in a known manner.

More preferably, the controller (40) is further configured to monitor the position and/or orientation of the patient's eye (1) while irradiating the diseased part of the patient's eye (1) with the particle beam (2), and to stop said irradiation as soon as the controller (40) detects or determines that the marker (30) is not (anymore) placed at the pre-determined and patient-specific position or that the patient's eye (1) is not gazing (anymore) at said marker (30). Stopping irradiation can for example be done by switching OFF the particle beam (2) in a known manner.

Preferably, the particle beam (2) is a beam of electrically charged particles, excluding electrons. More preferably, the particle beam (2) is a beam of protons or a beam of carbon ions. Preferably, the particle accelerator (3) is a cyclotron or a synchrotron, more preferably a synchrocyclotron, even more preferably a superconducting synchrocyclotron. Preferably, the particle accelerator (3) is adapted to generate and deliver at its output a beam of charged particles whose energy is higher than 60 MeV.

Preferably, the particle therapy apparatus further comprises a main energy degrader (80) placed across the beam line between an output of the particle accelerator (3) and the nozzle (4) and configured to vary the energy of the particle beam (2). In case the particle therapy apparatus comprises a rotatable gantry (20), the main energy degrader (80) is preferably arranged between an output of the particle accelerator (3) and entry point of the particle beam (2) into the rotatable gantry (20), as shown on FIG. 1.

The present invention has been described in terms of specific embodiments, which are illustrative of the invention and not to be construed as limiting.

Reference numerals in the claims do not limit their protective scope.

Use of the verbs "to comprise", "to include", "to be composed of", or any other variant, as well as their respective conjugations, does not exclude the presence of elements other than those stated. Use of the article "a", "an" or "the" preceding an element does not exclude the presence of a plurality of such elements.

The invention may also be described as follows: a particle therapy apparatus for irradiating a diseased part of a patient's eye (1) with a charged particle beam (2) comprises a particle accelerator (3) to generate the charged particle beam, a movable irradiation nozzle (4) adapted to direct the charged particle beam towards the patient's eye (1) according to different beam directions, and a patient support (5) adapted to receive and hold the patient in a treatment position. The apparatus further comprises a pencil beam scanning subsystem (10a, 10b) configured to scan the charged particle beam over the diseased part of the patient's eye (1), a movable marker (30) arranged in such a way that it is visible by the patient while the patient is in the treatment position, and a controller (40) configured to move said marker (30) to a pre-determined and patient-specific position before starting an irradiation of his eye (1) with the charged particle beam (2).

The invention claimed is:

1. A particle therapy apparatus for irradiating a diseased part of a patient's eye with a charged particle beam, comprising:
   a particle accelerator to generate the charged particle beam;
   a movable irradiation nozzle adapted to receive and direct the charged particle beam towards the patient's eye according to different beam directions;
   a patient support adapted to receive and hold the patient in a treatment position;
   a movable marker arranged in such a way that it is visible by the patient while the patient is in the treatment position;
   a controller configured to move said marker to a pre-determined and patient-specific position before an irradiation of the diseased part of the patient's eye with the charged particle beam; and
   a pencil beam scanning subsystem configured to scan the charged particle beam over the diseased part of the patient's eye.

2. A particle therapy apparatus according to claim 1, further comprising an isocentric gantry rotatable about an axis Y, said gantry comprising a sequence of bending magnets arranged along a beam path to receive the particle beam along the axis Y, to first bend the particle beam away from the axis Y and to finally bend and direct the particle beam back towards the axis Y, and in that the irradiation nozzle is arranged on said gantry and downstream of a last bending magnet of said sequence of bending magnets.

3. A particle therapy apparatus according to claim 1, wherein the pencil beam scanning subsystem is a spot scanning type subsystem.

4. A particle therapy apparatus according to claim 1, wherein the apparatus is configured to perform a complete irradiation treatment of the diseased part of the patient's eye with a single nominal beam direction with respect to a single direction of the optical axis of the patient's eye.

5. A particle therapy apparatus according to claim 1, wherein the movable marker is mechanically linked to the irradiation nozzle.

6. A particle therapy apparatus according to claim 1, wherein the movable marker comprises a light source, preferably a point source.

7. A particle therapy apparatus according to claim 1, wherein the patient support is adapted to receive and hold the patient in a supine treatment position or in a seated treatment position.

8. A particle therapy apparatus according to claim 1, wherein the irradiation nozzle comprises a collimator to reduce a lateral dose fall-off.

9. A particle therapy apparatus according to claim 1, wherein the apparatus further comprises a video camera placed in such a way that a field of view of said camera covers the patient's eye when the patient is in the treatment position, and in that the controller is further configured to acquire images from said video camera and to monitor the position and/or orientation of the patient's eye while the patient is in the treatment position.

10. A particle therapy apparatus according to claim 9, wherein the controller is further configured to monitor the position and/or orientation of the patient's eye before starting irradiation of the diseased part of the patient's eye with the particle beam, and to start said irradiation only when the controller detects that the marker is placed at the pre-determined and patient-specific position and that the patient's eye is gazing at said marker.

11. A particle therapy apparatus according to claim 9, wherein the controller is further configured to monitor the position and/or orientation of the patient's eye while irradiating the diseased part of the patient's eye with the particle beam, and to stop said irradiation as soon as the controller detects that the marker is not placed at the pre-determined and patient-specific position or that the patient's eye is not gazing at said marker.

12. A particle therapy apparatus according to claim 1, wherein the particle beam is a beam of electrically charged particles, excluding electrons, and preferably a beam of protons or a beam of carbon ions.

13. A particle therapy apparatus according to claim 1, wherein the particle accelerator is a cyclotron or a synchrotron.

14. A particle therapy apparatus according to claim 13, wherein the irradiation nozzle comprises an energy absorber to reduce the energy of the charged particle beam.

15. A particle therapy apparatus according to claim 14, wherein the energy absorber is configured to reduce the energy of the charged particle beam to less than 70 MeV at an output of the nozzle.

* * * * *